(12) United States Patent
Chen et al.

(10) Patent No.: US 6,392,053 B2
(45) Date of Patent: May 21, 2002

(54) PROCESS FOR PREPARING ARYLACETYLAMINOTHIAZOLES

(75) Inventors: Bang-Chi Chen, Plainsboro; Kyoung S. Kim, North Brunswick; S. David Kimball, East Windsor; Raj N. Misra, Hopewell, all of NJ (US); Joseph E. Sundeen, Yardley, PA (US); Rulin Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/746,059

(22) Filed: Dec. 22, 2000

Related U.S. Application Data

(63) Continuation-in-part of application No. 09/616,627, filed on Jul. 26, 2000, which is a continuation-in-part of application No. 09/616,629, filed on Jul. 26, 2000, now Pat. No. 6,214,852, which is a continuation-in-part of application No. 09/464,511, filed on Dec. 15, 1999, now Pat. No. 6,262,096.

(51) Int. Cl.$^7$ ............................................. C07D 417/12
(52) U.S. Cl. ...................................................... 548/185
(58) Field of Search ........................................ 548/185

(56) References Cited

U.S. PATENT DOCUMENTS

| 4,254,260 A | 3/1981 | Takaya ........................ 544/27 |
| 6,214,852 B1 | 4/2001 | Kim et al. |
| 2001/0006976 A1 | 7/2001 | Chen et al. |

FOREIGN PATENT DOCUMENTS

| EP | 0082498 B1 | 11/1989 |
| EP | 0625307 A1 | 11/1994 |
| EP | 0412404 B1 | 1/1996 |
| WO | WO 95/24403 | 9/1995 |
| WO | WO 96/17850 | 6/1996 |
| WO | WO 96/30370 | 10/1996 |
| WO | WO 97/29111 | 8/1997 |
| WO | WO 99/21845 | 5/1999 |
| WO | WO 99/24416 | 5/1999 |
| WO | WO 00/26202 | 5/2000 |
| WO | WO 01/44217 | 6/2000 |
| WO | WO 01/44242 | 6/2000 |
| WO | WO 01/44241 | 4/2001 |

OTHER PUBLICATIONS

T. Ogino et al., "Discovery of FR1115092: A Novel Antinephritic Agent"; Bioorg. & Med. Chem. Lett. 8 (1998) 75–80.

K. Tsuji et al., "Synthesis and Effects of Novel Thiazole Derivatives Against Thrombocytopenia"; Bioorg. & Med. Chem. Lett. 8 (1998) 2473–2478.

Baddi et al., "Synthesis and Antimicrobial Activity of Some Ethyl–2–amino/acetamido–5–arylthiothiazole–4–carboxylates and their sulphones: An attempted synthesis of 2–amino/acetamido[1]benzothiopyrano[3,2–d]thiazol–9(H)–ones"; Indian J. Chem. 35B (1996) 233–237.

Bellavita et al., Ann Chim. (Rome) 41, (1951) 194–198.
J. Am. Chem. Soc., vol. LXXI (1949) 4007–4010.
Behringer et al., Ann. Chem. 650 (1961) 179.
Scott et al., Applied Microbiology, vol. 10, pp. 211–216, 1962.
Hall et al., Journal of Heterocyclic Chemistry, vol. 29, No. 5, pp. 1245–1273, 1992.
Ganellin et al., Journal of Medicinal Chemistry, vol. 38, No. 17, pp. 3342–3350, 1995.
Smith et al., Heterocycles, vol. 37, No. 3, pp. 1865–1872, 1994.

Primary Examiner—Robert Gerstl
(74) Attorney, Agent, or Firm—Rena Patel

(57) ABSTRACT

The present invention relates to new, efficient processes for the preparation of 5-(2-oxazolylalkylthio)-2-arylacetylaminothiazole compounds of formula I

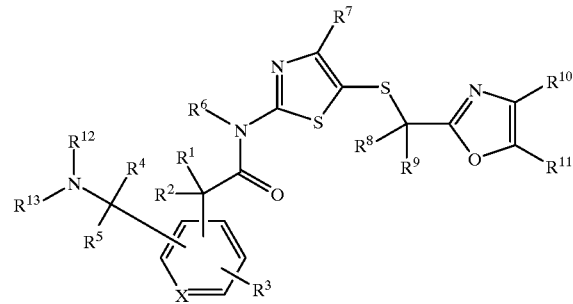

or a pharmaceutically acceptable salt thereof, wherein:
$R^1$, $R^2$, $R^4$, $R^5$, $R^6$, $R^8$, $R^9$, $R^{12}$ and $R^{13}$ are each independently hydrogen, alkyl, aryl or heteroaryl;
$R^3$, $R^7$, $R^{10}$ and $R^{11}$ are each independently hydrogen, alkyl, aryl, heteroaryl, halogen, hydroxy or alkoxy; and
X is CH or N,
which are novel, potent inhibitors of cyclin dependent kinases (cdks). The present invention also concerns a new process for the preparation of formylarylacetates and formylarylacetic acids.

26 Claims, No Drawings

PROCESS FOR PREPARING ARYLACETYLAMINOTHIAZOLES

CROSS-REFERENCE TO RELATED U.S. APPLICATIONS

This application is a continuation-in-part of (1) patent application Ser. No. 09/616,627, filed on Jul. 26, 2000 and (2) patent application Ser. No. 09/616,629, filed on Jul. 26, 200 now U.S. Pat. No. 6,214,852, which are continuation-in-part applications of patent application Ser. No. 09/464,511, filed Dec. 15, 1999 now U.S. Pat. No. 6,262,096.

STATEMENT REGARDING FEDERALLY SPONSORED RESEARCH OR DEVELOPMENT

Not Applicable

REFERENCE TO A "Microfiche Appendix"

Not Applicable

BACKGROUND OF THE INVENTION

1. Field of the Invention

The present invention concerns new processes for the preparation of 5-(2-oxazolylalkylthio)-2-arylacetylaminothiazoles and analogs, inhibitors of cyclin dependent kinases.

2. Description of the Related Art

The 5-(2-oxazolylalkylthio)-2-arylacetylaminothiazole compounds of formula I

I or a pharmaceutically acceptable salt thereof, wherein:

$R^1$, $R^2$, $R^4$, $R^5$, $R^6$, $R^8$, $R^9$, $R^{12}$ and $R^{13}$ are each independently hydrogen, alkyl, aryl or heteroaryl;

$R^3$, $R^7$, $R^{10}$ and $R^{11}$ are each independently hydrogen, alkyl, aryl, heteroaryl, halogen, hydroxy or alkoxy; and X is CH or N, are novel, potent inhibitors of cyclin dependent kinases (cdks). They are useful in the therapy of proliferative diseases, for example, cancer, inflammation, autoimmune diseases such as arthritis, viral diseases, fungal diseases, chemotherapy-induced alopecia, neurodegenerative disorders such as Alzheimer's disease and cardiovascular disease. More specifically, the compounds of formula I are useful in the treatment of a variety of cancers such as bladder, breast, colon, kidney, liver and lung cancers.

The preparation of 5-(2-oxazolylalkylthio)-2-aminothiazoles, key intermediates in the synthesis of 5-(2-oxazolylalkylthio)-2-arylacetylaminothiazoles of formula I, has been described (K. S. Kim et al., WO 9924416, May 20, 1999 and corresponding U.S. Pat. No. 6,040,321).

4-Formylphenylacetic acid has been previously prepared from ethyl phenylacetate in four steps which provided <15% overall yield (J. W. Baker et al., *J. Chem. Soc.* 1956, 404).

The reaction of 4-bromophenylacetic acid or ester with alkyl acrylates using palladium catalysts to give 4-(2-alkoxycarbonylvinyl)phenylacetic acid or ester has been previously reported in the literature (J. W. Tilley et al., *J. Med. Chem.* 1991, 34, 1125; A. Cerri et al., *J. Heterocycl Chem.* 1993, 30, 1581). The oxidation of β-arylacrylates to give aryl aldehydes has also been reported (G. Cainelli et al., *Synthesis*, 1989, 47; D. G. Lee et al., *Can. J. Chem.* 1972, 50; D. G. Lee et al., *Liebigs Ann. Chem.* 1993, 503; S. Antus et al., *Liebigs Ann. Chem.* 1993, 105).

BRIEF SUMMARY OF THE INVENTION

This invention concerns new efficient processes for the preparation of 5-(2-oxazolylalkylthio)-2-arylacetylaminothiazoles and analogs. The processes involve new strategy for the preparation of formylarylacetic acids, key intermediates in the synthesis of 5-(2-oxazolylalkylthio)-2-arylacetylaminothiazoles and analogs, inhibitors of cyclin dependent kinases.

BRIEF DESCRIPTION OF THE DRAWINGS

Not Applicable

DETAILED DESCRIPTION OF THE INVENTION

The present invention relates to new, more efficient processes for the preparation of formylarylacetic acids with application to the synthesis of 5-(2-oxazolylalkylthio)-2-arylacetylaminothiazoles and analogs, inhibitors of cyclin dependent kinases. The processes involve reaction of haloarylacetic acids or esters II with olefins III to give vinylarylacetic acids or esters IV. Oxidation of IV with an oxidizing reagent gives formylarylacetic acids or esters V. Compared to the previous process which takes four steps and has yields less than 15%, the process of the invention can obtain the formylacetic acids or esters in only two steps and at substantially higher yields.

Subsequent coupling of formylarylacetic acids or esters V with 5-(2-oxazolylalkylthio)-2-aminothiazoles VI produces amides VII. Reductive amination of the amide VII with amines affords 5-(2-oxazolylalkylthio)-2-(aminoalkyl) arylacetylaminothiazoles I, inhibitors of cyclin dependent kinases.

Alternatively, compounds of formula I can be prepared by coupling of haloalkylarylacetic acids VIII with 5-(2-oxazolylalkylthio)-2-aminothiazoles VI followed by aminolysis of the resulting amides IX with amines.

The above-described reactions are illustrated in the below Scheme 1.

Scheme 1

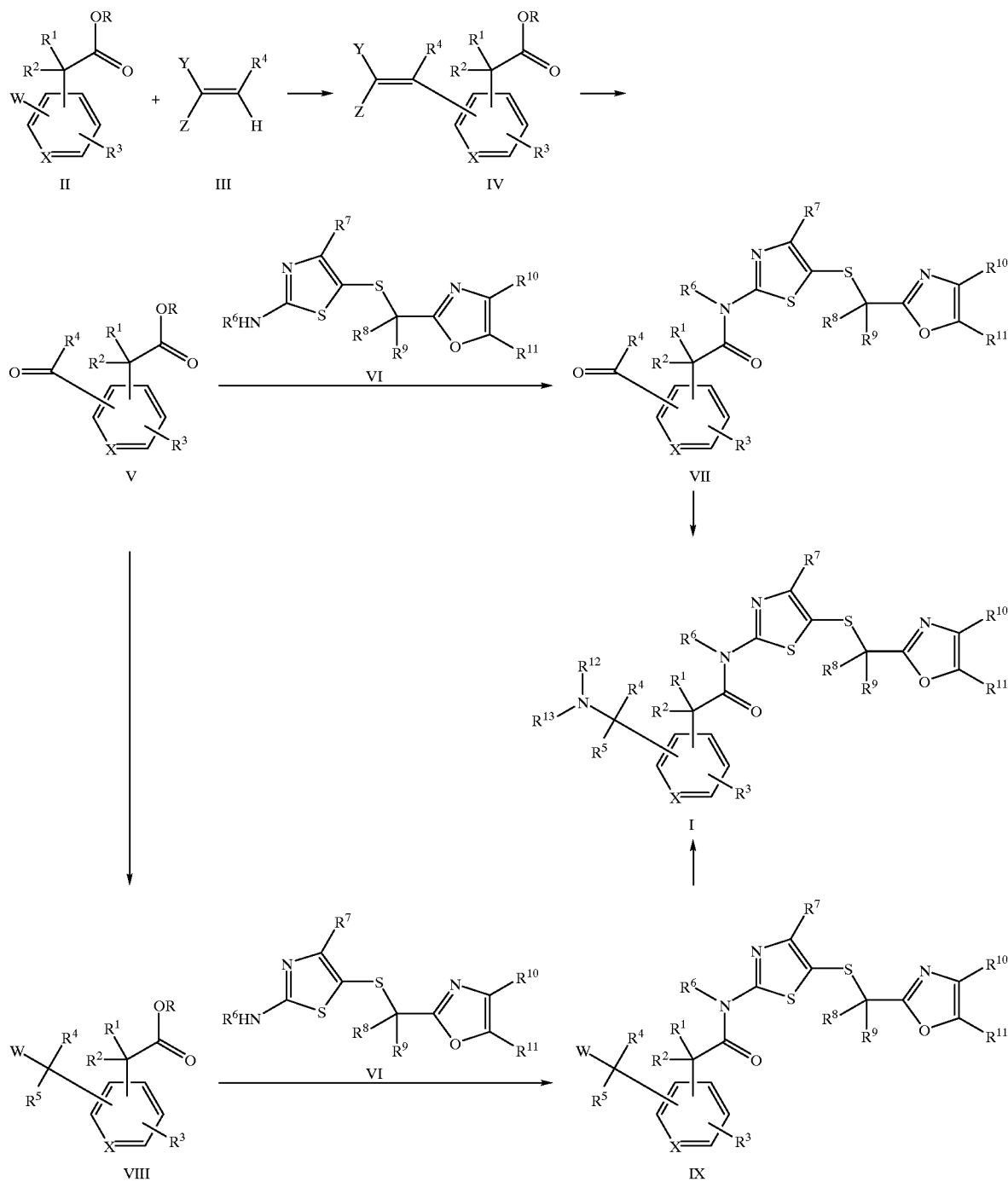

In formulas I–IX of Scheme 1, the following terms apply:
R, $R^1$, $R^2$, $R^4$, $R^5$, $R^6$, $R^8$, $R^9$, $R^{12}$ and $R^{13}$ are each independently hydrogen, alkyl, aryl or heteroaryl;
$R^3$, $R^7$, $R^{10}$ and $R^{11}$ are each independently hydrogen, alkyl, aryl, heteroaryl, halogen, hydroxy or alkoxy;
W is halogen or sulfonate ($RSO_2O$—, $CF_3SO_2O$—, etc.);
X is CH or N;
Y is CHO, C(O)R, COOR, $CONRR^1$, CN, $NO_2$, $SO_2OR$ or $SO_2NRR^1$; and
Z is hydrogen, CHO, C(O)R, COOR, $CONRR^1$, CN, $NO_2$, $SO_2OR$ or $SO_2NRR^1$.

Listed below are definitions of various terms used to describe the compounds involved in the processes of the present invention. These definitions apply to the terms as they are used throughout the specification (unless specifically indicated otherwise) either individually or as part of a larger group. It should be noted that any heteroatom with unsatisfied valences is assumed to have the hydrogen atom to satisfy the valences.

The term "alkyl" or "alk" (i.e., derivative forms of alkyl) refers to optionally substituted straight chain, branched or cyclic monovalent alkane (saturated hydrocarbon) derived radicals containing from 1 to 12 carbon atoms. When substituted, alkyl groups may be substituted with up to four substituent groups at any available point of attachment. Examples of alkyl groups include, but are not limited to, methyl, ethyl, propyl, isopropyl, n-butyl, t-butyl, isobutyl, pentyl, hexyl, isohexyl, heptyl, octyl, nonyl, decyl, undecyl, dodecyl and the like. The alkyl can be optionally substituted with one or more halogens or alkyl groups such as, for example, trifluoromethyl, 4,4-dimethylpentyl, 2,2,4-trimethylpentyl, etc.

The term "aryl" or derivative forms thereof refers to monocyclic or bicyclic aromatic rings, e.g., phenyl, substituted phenyl and the like, as well as groups which are fused, e.g., napthyl, phenanthrenyl and the like, containing from 6 to 30 carbon atoms. An aryl group can thus contain at least one ring having 6 atoms, with up to five such rings being present, containing up to 22 or 30 atoms therein, depending upon optionally alternating (resonating) double bonds between carbon atoms or suitable heteroatoms. Examples of aryl groups include, but are not limited to, phenyl, naphthyl, anthryl, biphenyl and the like.

The term "halogen" or "halo" refers to chlorine, bromine, fluorine or iodine, with bromine being the preferred halogen. The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Exemplary heteroaryl groups include, but are not limited to, thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, pyridazinyl, pyrimidinal triazinylazepinyl, indolyl, isoindolyl, quinolinyl, isoquinolinyl, benzothiazolyl, benzoxazolyl, benzimidazolyl, benzoxadiazolyl, benzofurazanyl, etc. The heteroaryl groups can be optionally substituted by one or more groups which include, but are not limited to, halogen, alkyl, alkoxy, hydroxy, carboxy, carbamoyl, alkyloxycarbonyl, trifluoromethyl, cycloalkyl, nitro, cyano, amino, alkylS(O)$_m$ (where m=0, 1 or 2), thiol and the like.

The term "pharmaceutically acceptable salt" refers to those salts of the biologically active compounds which do not significantly or adversely affect the pharmaceutical properties of the compounds, such as, for example, toxicity, efficacy, etc. and include those salts which are conventionally employed in the pharmaceutical industry. Suitable examples of salts include, but are not limited to, those formed with inorganic or organic acids such as hydrochloride, hydrobromide, sulfate, phosphate, etc. Also included, particularly for the intermediate compounds of the invention, are salts which are unsuitable for pharmaceutical utility but which can be employed otherwise, for example, for isolation or purification of free active compounds or their pharmaceutically acceptable salts.

All stereoisomers of the compounds of the instant invention are contemplated, either in admixture or in pure or substantially pure form. The definition of the compounds employed in the processes of the invention embraces all possible stereoisomers and their mixtures. The definition further embraces the racemic forms and the isolated optical isomers having the specified activity. The racemic forms can be resolved by physical methods such as, for example, fractional crystallization, separation or crystallization of diastereomeric derivatives or separation by chiral column chromatography. The individual optical isomers can be obtained from the racemates by conventional methods such as, for example, salt formation with an optically active acid followed by crystallization.

It should be understood that solvates (e.g., hydrates) of the compounds of formula I and the intermediate compounds are also within the scope of the present invention. Methods of solvation are generally known in the art. Therefore, the compounds useful in the processes of this invention may be in the free or hydrate form.

As set forth in Scheme 1, the process for the preparation of 5-(2-oxazolylalkylthio)-2-arylacetylaminothiazoles and analogs involves the following transformations:

(a) reacting a haloarylacetate II with an olefin III in the presence of a palladium catalyst in a suitable solvent or solvent mixtures to give a vinyl-substituted arylacetate IV such as vinylarylacetate.

It should be appreciated that the term "haloarylacetate" for purposes of the present invention includes both haloarylacetic acids and esters. Additionally, a sulfonate, for example, RSO$_2$O— (where R is alkyl, aryl or heteroaryl), CF$_3$SO$_2$O— and the like, may be substituted for the halogen in the arylacetate or arylacetic acid starting compounds. The preferred haloarylacetates are haloarylacetic acids with bromophenylacetic acids, such as, for example, 4-bromophenylacetic acid, most preferred. The olefin includes alkenes and polymers derived from an alkene such as ethyl or methyl acrylate. The palladium catalysts include, but are not limited to, palladium acetate or diacetate, palladium halides, etc., with the palladium diacetate preferred. Other standard catalysts may be employed although less conveniently. A conventional ligand for the palladium catalyst such as trialkyl or triarylphosphine can also be employed. Suitable solvent(s) include solvents such as hydrocarbons, ethers, amides, for example, dimethylformamide ("DMF"), ketones, etc., or mixtures thereof, with amides such as DMF preferred.

(b) reacting the vinyl-substituted arylacetate IV, like vinylarylacetate, obtained in step (a) with an oxidizing reagent in a suitable solvent or solvent mixtures to give a formylarylacetate V.

The oxidizing reagent includes, but is not limited to, O$_3$, KMnO$_4$, NaIO$_4$/OsO$_4$, etc., with NaIO$_4$/OsO$_4$ preferred. Suitable solvent(s) include solvents such as hydrocarbons, ethers, esters, amides, and the like, mixtures thereof, or aqueous mixtures thereof, with an ether and water mixture preferred.

For example, the oxidative cleavage of the double bond of formula IV by a reagent such as osmium tetroxide with sodium periodate in a dioxane/water mixture gives the desired vinyl-substituted arylacetic acid or arylacetate, such as formylphenylacetic acid or formylphenylacetate.

(c) reacting the formylarylacetate V obtained in step (b) with a 5-(2-oxazolylalkylthio)-2-aminothiazole compound VI in the presence of a coupling reagent and in a suitable solvent or solvent mixtures to give an amide VII.

The 5-(2-oxazolylalkylthio)-2-aminothiazoles include 5-(5-substituted-2-oxazolylalkylthio)-2-aminothiazole compounds with 5-(5-t-butyl-2-oxazolylalkylthio)-2-aminothiazole preferred. The coupling reagents include, but are not limited to, carbodiimides, haloformates, thionyl halide and the like, with thionyl halide preferred. Suitable solvent(s) include aprotic solvents such as hydrocarbons, halogenated hydrocarbons, ethers, esters, etc., with halogenated hydrocarbons such as dichloromethane preferred.

(d) reacting the amide VII obtained in step (c) with an amine in the presence of a reducing reagent in a suitable solvent or solvent mixtures to give 5-(2-oxazolylalkylthio)-2-(aminoalkyl) arylacetylaminothiazole I.

The amine used in reaction (d) includes primary and secondary amines with primary aliphatic amines preferred. The reducing reagents include, but are not limited to, $NaBH_4$, $NaBH(OAc)_3$, $Et_3SiH/TFA$ and the like with $NaBH(OAc)_3$ preferred. Suitable solvent(s) include hydrocarbons, halogenated hydrocarbons, ethers, esters, etc., or mixtures thereof, with ethers such as tetrahydrofuran ("THF") preferred.

Alternatively, the compounds of formula I can be prepared by:

(c') reacting the haloalkylarylacetate VIII with a 5-(2-oxazolylalkylthio)-2-aminothiazole compound VI in the presence of a coupling reagent and in a suitable solvent or solvent mixtures to give an amide IX.

The 5-(2-oxazolylalkylthio)-2-aminothiazoles include 5-(5-substituted-2-oxazolylalkylthio)-2-aminothiazole compounds with 5-(5-t-butyl-2-oxazolylalkylthio)-2-aminothiazole preferred. The coupling reagents include, but are not limited to, carbodiimides, haloformates, thionyl halide and the like, with the former preferred, for example, an alkylcarbodiimide. Suitable solvent(s) include aprotic solvents such as hydrocarbons, halogenated hydrocarbons, ethers, esters, etc., with halogenated hydrocarbons such as dichloromethane preferred.

For instance, treatment of haloalkylarylacetate or haloalkylarylacetic acid VIII such as haloalkylphenylacetate or haloalkylphenylacetic acid with 5-(2-oxazolylalkylthio)-2-aminothiazole VI provides a haloalkyl-substituted phenylacetamide IX.

(d') reacting the amide IX obtained in step (c') with an amine in a suitable solvent or solvent mixtures to give 5-(2-oxazolylalkylthio)-2-(aminoalkyl) arylacetylaminothiazole The amine used in reaction (d') includes primary and secondary amines with primary aliphatic amines preferred. Suitable solvent(s) include hydrocarbons, halogenated hydrocarbons, ethers, esters, amides, etc., with amides such as DMF preferred.

For example, the reaction under reductive amination conditions with a primary or secondary amine in the presence of sodium cyanoborohydride or hydrogen in the presence of a catalyst gives the compounds of formula I.

Alternatively, the aldehydes of formula VII may be reacted with an organometallic reagent such as methylmagnesium bromide in a suitable solvent or solvent mixture, such as, for example, ether to give an alcohol derivative. The alcohol derivative is converted to its corresponding halide such as a chloride by a chlorinating agent such as thionyl chloride. The halide compound such as the chloride compound may then be converted to a compound of formula I by reaction with an excess of a primary or secondary amine in a suitable solvent such as ethanol.

The starting compounds of Scheme 1 are commercially available or may be prepared by methods known to one of ordinary skill in the art.

To further illustrate Scheme 1, a process to make formylphenylacetic acids with application to the synthesis of 5-(5-t-butyl-2-oxazolylmethylthio)-2-[(aminomethyl) phenylacetyl]aminothiazoles and analogs thereof, for example, starts with the reaction of halophenylacetic acids II such as bromophenylacetic acid ($R=R^1=R^2=R^3=H$, $X=Br$) with alkyl acrylate III such as ethyl acrylate ($R^4=Z=H$, $Y=CO_2Et$) to give (2-ethoxycarbonyl) vinylphenylacetic acids IV ($R=R^1=R^2=R^3=R^4=Z=H$, $Y=CO_2Et$). Oxidation of IV with a suitable oxidizing reagent gives formylphenylacetic acids V ($R=R^1=R^2=R^3=R^4=H$). Coupling of V with 5-(5-t-butyl-2-oxazolylalkylthio)-2-aminothiazole VI ($R^6=R^7=R^8=R^9=R^{10}=H$, $R^{11}=$t-Bu) produces amides VII ($R^1=R^2=R^3=R^4=R^6=R^7=R^9=R^{10}=H$, $R^{11}=$t-Bu). Reductive amination of VI amines affords 5-(5-t-butyl-2-oxazolylalkylthio)-2-(aminomethyl) phenylacetylaminothiazoles I, inhibitors of cyclin dependent kinases. Alternatively, compounds of formula I can be prepared by coupling of haloalkylphenylacetic acids VIII such as bromomethylphenylacetic acid ($R=R^1=R^2=R^3=R^4=R^5=H$) with 5-(5-t-butyl-2-oxazolylalkylthio)-2-aminothiazole VI followed by aminolysis of the resulting amides IX with amines.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples which follow below.

EXAMPLE 1

A. Preparation of 4-[2-(Ethoxycarbonyl)vinyl] phenylacetic Acid

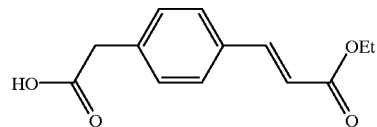

To a stirred solution of 4-bromophenylacetic acid (43.0 g, 200 mmol) in dimethyl formamide (400 mL) in a round bottom flask under nitrogen atmosphere at room temperature was added ethyl acrylate (43.3 mL, 400 mmol), palladium diacetate (0.90 g, 4 mmol), triphenylphosphine (2.10 g, 8 mmol), and diisopropylethylamine (87.2 mL, 500 mmol). The reaction mixture was heated to 100° C. for 43 hours, cooled to room temperature, and hydrochloric acid (1N, 1 L) was added. To the reaction mixture was added ethyl acetate (500 mL), the aqueous layer was extracted with ethyl acetate (2×500 mL), and the combined organic layers washed with hydrochloric acid (1N, 500 mL), water (500 mL) and saturated sodium chloride solution (250 mL), then dried over sodium sulfate, filtered and evaporated in vacuo to provide the title compound as a mixture of cis and trans isomers (46.9 g, 100%).

EXAMPLE 2

B. Preparation of 4-Formylphenylacetic Acid

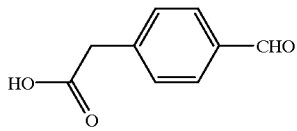

To a stirred solution of the title compound of Example 1 (46.9 g, 200 mmol) in dioxane (500 mL) and water (500 mL) was added osmium tetroxide (0.5 g, 4% in water), followed by sodium periodate (85.56 g, 400 mmol). The reaction mixture was monitored by HPLC, stirred for 1 hour and N-methylmorpholine (1.0 g) was added, followed by additional osmium tetroxide (1.0 g) after another 16 hours. After 4 hours stirring at room temperature, additional sodium periodate (40 g) was added, the reaction stirred for 21 hours, filtered, and the filter cake washed with ethyl acetate (500 mL). The phases were separated, the aqueous layer extracted with ethyl acetate (500 mL), the remaining aqueous layer acidified with hydrochloric acid (30 mL), extracted with ethyl acetate (500 mL), and the combined organic phases washed with water (500 mL), saturated sodium chloride solution (250 mL), dried over sodium sulfate, filtered and the solvent removed in vacuo. The wet solid was triturated with methyl tert-butyl ether (50 mL) and to the resulting slurry was added pentane (100 mL). The slurry was filtered, the solid product was washed with pentane (2×25 mL) and dried to give the title compound (12.4 g, 38%). HPLC: 2.19 min (YMC S5 ODS column 4.6×50 mm, 10–90% aqueous methanol over 4 minutes containing 0.2% phosphoric acid, 4 mL/min, monitoring at 220 nm). $^1$H NMR ($d_6$-DMSO): δ 9.99 (s, 1H), 7.85–7.87 (d, 2H), 7.49–7.51 (d, 2H); 3.72 (s, 3H).

EXAMPLE 3

C. Preparation of 5-(5-t-Butyl-2-oxazolylalkylthio)-2-(4-formylphenyl)-acetylaminothiazole

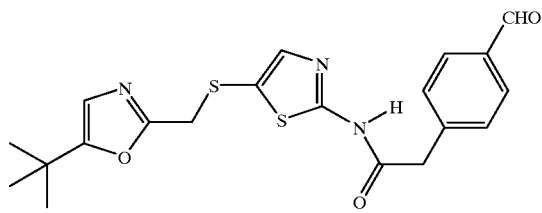

Oxalyl chloride (2.0 M in $CH_2Cl_2$, 9.1 mL, 18.2 mmol, 3 eq) was added slowly to a solution of the title compound of Example 2 (2.0 g, 12.2 mmol, 2 eq) in $CH_2Cl_2$ at 0° C. The resultant acyl chloride containing reaction mixture was added to a solution of 2-amino-5-[[[5-(1,1-dimethylethyl)-2-oxazolyl]methyl]thio]thiazole dropwise (1.64 g, 6.09 mmol) and triethylamine (3.2 mL) in dichloromethane. The reaction was stirred at 0° C. for 5 minutes and then allowed to warm to room temperature. After 30 minutes, saturated aqueous $NaHCO_3$ was added with $CH_2Cl_2$ (220 mL), the organic extract washed with saturated aqueous $NaHCO_3$, 0.1N HCl, saturated NaCl, and dried over $MgSO_4$. Concentration in vacuo gave a brown oil which was triturated with hexane followed by ethyl acetate to provide 1.03 g of yellowish solid. An additional 1.02 g of material was obtained from the filtrate by flash chromatography on silica gel eluting with a gradient of 50–60% ethyl acetate in hexane to provide a total of 2.05 g (81%) of the title compound. HPLC: 97% at 3.90 min (YMC S5 ODS column 4.6×50 mm, 10–90% aqueous methanol over 4 minutes containing 0.2% phosphoric acid, 4 mL/min, monitoring at 220 nm).

EXAMPLE 4

D. Preparation of 5-(5-t-Butyl-2-oxazolylalkylthio)-2-[4-(3-hydroxy-2,2-dimnethylpropylaminomethyl)phenyl]acetylaminothiazole

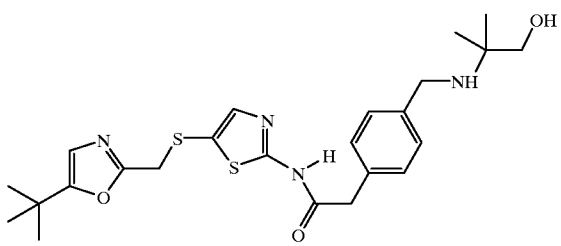

To the title compound of Example 3 (1.1 g, 2.65 mmol, 1 eq) dissolved in 20 mL of tetrahydrofuran and cooled to 0° C. was added 3-amino-2,2-dimethyl-1-propanol (1.0 g, 9.7 mmol, 3.7 eq), followed by acetic acid (1 mL) and sodium triacetoxyborohydride (2.6 g, 12.3 mmol, 4.6 eq). The reaction was stirred at room temperature for 1 hour. Aqueous $NaHCO_3$ was added, and the mixture was extracted with ethyl acetate. The organic extracts were washed with water, dried over $MgSO_4$, and concentrated in vacuo. The material was acidified by addition of 4N HCl in dioxane to a solution in methanol. The product was also purified by flash chromatography on silica gel eluting with 10% methanol in ethyl acetate with 2.7% triethylamine to provide 530 mg (40%) of the title compound as a beige solid. HPLC: 97% at 3.28 min (YMC S5 ODS column 4.6×50 mm, 10–90% aqueous methanol over 4 minutes containing 0.2% phosphoric acid, 4 mL/min, monitoring at 220 nm).

EXAMPLE 5

C' Preparation of 5-(5-t-Butyl-2-oxazolylalkylthio)-2-(4-bromomethylphenyl)acetylaminothiazole

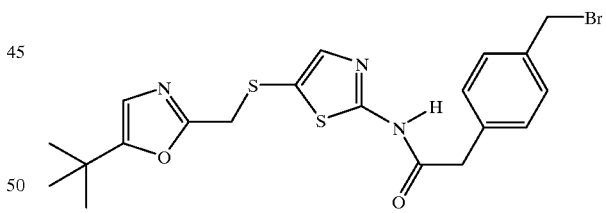

1,3-Dicyclohexylcarbodiimide (7.18 g, 34.8 mmol, 1.25 eq) was added to a mixture of 5-(5-t-butyl-2-oxazolylalkylthio)-2-aminothiazole (7.5 g, 27.8 mmol, 1 eq) and 4-bromomethylphenylacetic acid (7.97 g, 34.8 mmol, 1.25 eq) in 175 mL of $CH_2Cl_2$ at 0° C. The reaction mixture was allowed to warm to room temperature. After 30 minutes LC/MS indicated that the reaction was complete, the mixture was filtered and concentrated in vacuo onto 20 g of silica gel. The material was purified by flash chromatography on silica gel eluting with 60% ethyl acetate in hexane to provide 11.5 g (83%) of the title compound as a yellow solid.

In an alternative method of preparation, 1-(3-dimethylaminopropyl)-3-ethylcarbodiimide hydrochloride (13.8 g, 72 mmol, 2 eq) was added to a mixture of 5-(5-t-butyl-2-oxazolylalkylthio)-2-aminothiazole (2.0 g, 7.42 mmol, 1 eq) and 4-bromomethyl phenylacetic acid (2.60 g, 11.3 mmol, 1.5 eq) in CH$_2$Cl$_2$ (30 mL) under N$_2$ at room temperature. After 1 hour, the reaction was diluted with 20 mL of ethyl acetate and washed with saturated aqueous NaHCO$_3$ (2×20 mL). The organic phase was then washed with 10% aqueous citric acid, dried over MgSO$_4$, and concentrated in vacuo to provide a yellow solid. This material was triturated with ether to provide 3.01 g (84.4%) of the title compound. HPLC: R.T.=3.693 min (YMC S5 ODS column 4.6×50 mm, 10–90% aqueous methanol over 4 minutes containing 0.2% phosphoric acid, 4 mL/min, monitoring at 220 nm); $^1$H NMR (CDCl$_3$): δ 7.37–7.24 (m, 5H), 6.54 (s, 1H), 4.47 (s, 2H), 3.93 (s, 2H), 3.79 (s, 2H), 1.27 (s, 9H).

EXAMPLE 6

D' Preparation of 5-(5-t-Butyl-2-oxazolylalkylthio)-2-[4-(aminomethyl)phenyl]-acetylaminothiazole

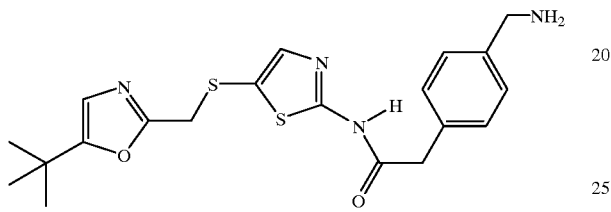

The title compound of Example 5 (70% pure, 1.05 g, 1.53 mmol, 1 eq) was dissolved in 40 mL of N,N-dimethylformamide and cooled to –70° C. Excess liquid ammonia (6 mL) was added, and after sealing the reaction vessel, the mixture was allowed to warm to room temperature. After 1 hour, the reaction was diluted with ethyl acetate, washed with water (20 mL) and saturated aqueous NaCl, dried over MgSO$_4$, and concentrated in vacuo. The resulting yellow oil was purified by preparative HPLC to provide 270 mg (42.4%) of the title compound. HPLC R.T.=3.17 min (YMC S5 ODS column 4.6×50 mm, 10–90% aqueous methanol over 4 minutes containing 0.2% phosphoric acid, 4 mL/min, monitoring at 220 nm).

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:
1. A process for the preparation of a compound having the formula I

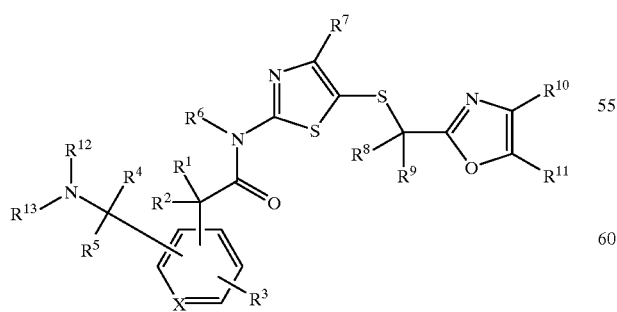

I or a pharmaceutically acceptable salt thereof, wherein:
R$^1$, R$^2$, R$^4$, R$^5$, R$^6$, R$^8$, R$^9$, R$^{12}$ and R$^{13}$ are each independently hydrogen, alkyl, aryl or heteroaryl;

R$^3$, R$^7$, R$^{10}$ and R$^{11}$ are each independently hydrogen, alkyl, aryl, heteroaryl, halogen, hydroxy or alkoxy; and
X is CH or N;
which comprises the steps of:
(a) reacting an arylacetate or an arylacetic acid having the formula II

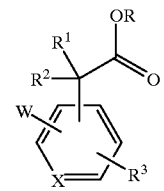

II wherein:
R$^1$, R$^2$, R$^3$ and X are as described hereinabove;
R is hydrogen, alkyl, aryl or heteroaryl; and
W is halogen or sulfonate;
with an olefin having the formula III

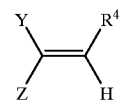

III wherein:
Y is CHO, C(O)R, COOR, CONRR$^1$, CN, NO$_2$, SO$_2$OR or SO$_2$NRR$^1$;
Z is hydrogen, CHO, C(O)R, COOR, CONRR$^1$, CN, NO$_2$, SO$_2$OR or SO$_2$NRR$^1$; and
R, R$^1$ and R$^4$ are as described hereinabove;
in the presence of a palladium catalyst in a suitable solvent or solvent mixture to form a vinyl-substituted arylacetate or vinyl-substituted arylacetic acid;
(b) reacting the vinyl-substituted arylacetate or vinyl-substituted arylacetic acid with an oxidizing reagent in a suitable solvent or solvent mixture to form a formylarylacetate or formylarylacetic acid compound;
(c) reacting the formylarylacetate or formylarylacetic acid compound with a 5-(oxazolylalkylthio)-2-aminothiazole compound having the formula VI

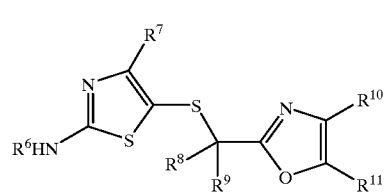

VI wherein:
R$^6$, R$^7$, R$^8$, R$^9$, R$^{10}$ and R$^{11}$ are as described hereinabove;
in the presence of a coupling reagent in a suitable solvent or solvent mixture to form an amide; and
(d) reacting the amide with an amine in the presence of a reducing reagent in a suitable solvent or solvent mixture to form the compound of formula I.

2. The process as recited in claim 1, wherein the arylacetate or the arylacetic acid in step (a) is a haloarylacetate or a haloarylacetic acid.

3. The process as recited in claim 2, wherein the haloarylacetic acid is a bromoarylacetic acid.

4. The process as recited in claim 3, wherein the bromoarylacetic acid is 4-bromophenylacetic acid.

5. The process as recited in claim 1, wherein the olefin in step (a) is an alkyl acrylate.

6. The process as recited in claim 1, wherein the palladium catalyst in step (a) is palladium acetate, palladium diacetate or palladium halide.

7. The process as recited in claim 6, wherein the palladium catalyst is palladium diacetate.

8. The process as recited in claim 1, wherein the solvent in step (a) is a hydrocarbon, an ether, an amide, a ketone or a mixture thereof.

9. The process as recited in claim 8, wherein the solvent is the amide and the amide is dimethylformamide.

10. The process as recited in claim 1, wherein step (a) forms a vinylarylacetate or a vinylarylacetic acid.

11. The process as recited in claim 1, wherein the oxidizing reagent in step (b) is $O_3$, $KMnO_4$ or $NaIO_4/OsO_4$.

12. The process as recited in claim 11, wherein the oxidizing reagent is $NaIO_4/OsO_4$.

13. The process as recited in claim 1, wherein the solvent in step (b) is a hydrocarbon, an ether, an ester, an amide, a mixture thereof or an aqueous mixture thereof.

14. The process as recited in claim 13, wherein the solvent is the aqueous mixture of an ether and water.

15. The process as recited in claim 1, wherein the 5-(2-oxazolylalkylthio)-2-aminothiazole compound in step (c) is a 5-(5-substituted-2-oxazolylalkylthio)-2-aminothiazole compound.

16. The process as recited in claim 15, wherein the 5-(5-substituted-2-oxazolylalkylthio)-2-aminothiazole compound is 5-(5-t-butyl-2-oxazolylalkylthio)-2-aminothiazole.

17. The process as recited in claim 1, wherein the coupling reagent in step (c) is a carbodiimide, a haloformate or a thionyl halide.

18. The process as recited in claim 17, wherein the coupling reagent is the thionyl halide.

19. The process as recited in claim 1, wherein the solvent in step (c) is a hydrocarbon, a halogenated hydrocarbon, an ether, an ester or a mixture thereof.

20. The process as recited in claim 19, wherein the solvent is the halogenated hydrocarbon and the halogenated hydrocarbon is dichloromethane.

21. The process as recited in claim 1, wherein the amine in step (d) is a primary amine or a secondary amine.

22. The process as recited in claim 21, wherein the amine is the primary amine and the primary amine is a primary aliphatic amine.

23. The process as recited in claim 1, wherein the reducing reagent in step (d) is $NaBH_4$, $NaBH(OAc)_3$ or $Et_3SiH/TFA$.

24. The process as recited in claim 23, wherein the reducing reagent is $NaBH(OAc)_3$.

25. The process as recited in claim 1, wherein the solvent in step (d) is a hydrocarbon, a halogenated hydrocarbon, an ether, an ester or a mixture thereof.

26. The process as recited in claim 25, wherein the solvent is the ether and the ether is tetrahydrofuran.

* * * * *